United States Patent [19]

Virgilio et al.

[11] 4,281,136

[45] Jul. 28, 1981

[54] 2-ALKYL-3-HALOISOTHIAZOLIUM SALTS AND THEIR DERIVATIVES

[75] Inventors: Joseph A. Virgilio; Milton Manowitz, both of Wayne; Emanuel Heilweil, Fairfield, all of N.J.

[73] Assignee: Givaudan Corporation, Clifton, N.J.

[21] Appl. No.: 952,038

[22] Filed: Oct. 16, 1978

Related U.S. Application Data

[63] Continuation-in-part of Ser. No. 854,456, Nov. 25, 1977, abandoned.

[51] Int. Cl.$^3$ ................. C07D 275/02; A61K 31/424
[52] U.S. Cl. ..................................... 548/206; 548/213; 548/214; 548/101; 424/290
[58] Field of Search ............... 260/302 A, 302 E, 299; 548/206, 213, 214, 101

[56] References Cited

U.S. PATENT DOCUMENTS 3,761,488  9/1973  Lewis et al. ............. 260/302 A

*Primary Examiner*—Donald G. Daus
*Assistant Examiner*—D. B. Springer
*Attorney, Agent, or Firm*—Robert F. Tavares; Thomas Cifelli, Jr.

[57] ABSTRACT

This disclosure relates to a novel class of 2-alkyl-3-haloisothiazolium salts. These salts have been found to be useful in controlling the growth of bacteria and fungi. They have also been found to be useful intermediates in the preparation of novel and known antibacterial and antifungal compounds.

44 Claims, No Drawings

2-ALKYL-3-HALOISOTHIAZOLIUM SALTS AND THEIR DERIVATIVES

RELATED U.S. APPLICATION DATA

This is a continuation-in-part of Ser. No. 854,456 filed Nov. 25, 1977, now abandoned.

BACKGROUND OF THE INVENTION

1. Field of the Invention

Antibacterial and Antifungal Compositions

2. Prior Art

The 2-alkyl-3-haloisothiazolium salts of this invention are novel compounds. The 2-alkyl-4-isothiazolin-3-thiones and 2-alkyl-3-dicyanomethylene-4-isothiazolines produced therefrom are also novel.

The 2-alkyl-3-haloisothiazolium salts can be converted to 2-alkyl-4-isothiazolin-3-ones. A number of these 2-alkyl-4-isothiazolin-3-ones have been reported in the literature; U.S. Pat. No. 3,761,488; J. Heterocyclic Chem. 8, 571 (1971).

SUMMARY OF THE INVENTION

The novel 2-alkyl-3-haloisothiazolium salts disclosed herein can be represented by the general formula:

Formula I

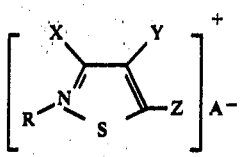

wherein

R represents an alkyl or alkenyl group;

X represents a halogen, preferably chlorine or bromine;

Y and Z represent suitable substituents as defined herein; and $A^-$ represents a suitable anion as defined herein.

These novel salts are useful as antibacterial and antifungal agents and find utility in paints, polymer emulsions, paper mills, industrial cooling water, agriculture, soaps, cutting oils, anionic surfactants, adhesives etc. They may be used alone or in admixture with other antimicrobial agents.

The novel 2-alkyl-3-haloisothiazolium salts are also useful intermediates in the manufacture of other valuable antimicrobial agents. These salts can be reacted with a variety of reagents to provide the transformations which are illustrated as follows:

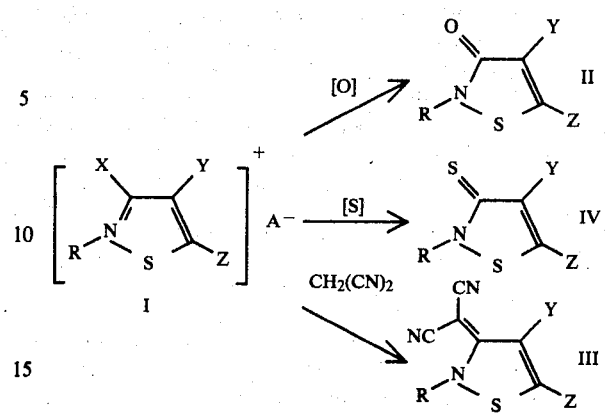

wherein [O] is a suitable oxygen source and [S] is a suitable sulfur source as described herein.

The 2-alkyl-3-haloisothiazolium salts of this invention are prepared by reacting the corresponding 3-haloisothiazoles with a suitable alkylating agent as illustrated below.

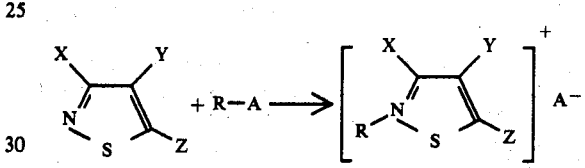

The starting 3-haloisothiazoles can be prepared by methods known in the art (W. R. Hatchard, J. Org. Chem., 29, 660 (1964); S. Nakagawa, J. Okumura, F. Sakai, H. Hoshi and T. Naito, Tetrahederon Letters, 3719 (1970); R. P. Williams, U.S. Pat. No. 3,285,390; and E. Mailey, U.S. Pat. No. 3,341,547).

DESCRIPTION OF THE PREFERRED EMBODIMENTS

The salts of formula I, more particularly the cations thereof, are the essence of this invention. They are useful to control the growth of bacteria and, or fungi and they are useful intermediates in the synthesis of other antibacterial and antifungal agents.

It is the cationic portion which is essential for the antimicrobial activity demonstrated by the salts and it is the cationic portion that is a precursor for the synthesis of other antimicrobial compounds.

The anionic portion of formula I is not critical and its sole purpose, insofar as is pertinent to this invention, is to neutralize the charge of the cation. The nature of the anion does not materially effect the antimicrobial activity of the cation nor does the anion affect the utility of the salts as intermediates in the preparation of the other antimicrobials II, III and IV. It is not impossible, however, that the anion might play a role in special applications where differences such as stability, solubility or some unique physical property may be significant or where the anion is a special negatively charged species which itself has antimicrobial activity.

In formula I, X represents a halogen. While any halogen may be suitable, those salts wherein X is bromine or chlorine are preferred because of their economy and availability. Compounds wherein X is chlorine are the most economical and are especially preferred.

The substituents Y and Z can be the same or different. They are preferably chosen from the group consisting of hydrogen, lower alkyl (e.g. methyl to butyl with methyl and ethyl being especially preferred) halogen (F, Cl, Br or I with Cl being especially preferred), cyano, carboalkoxy (e.g. carbomethoxy through carbobutoxy with carbomethoxy and carboethoxy being especially preferred). While variation in Y and Z do appear to have some effect on the level of activity, that effect is one of degree rather than one of kind. In all cases tested the level of activity exceeded the level desirable for commercial purposes. The preferences for one group over another, in the final analysis would most probably be governed by economic factors related to ease of synthesis, cost of materials etc.

The size of the R group is not critical. Any alkyl or alkenyl group is deemed suitable. The groups may be normal or branched and may be alicyclic or cyclic. As a practical matter, groups having eight carbons or less are preferred (e.g. alkyl groups from methyl to octyl and alkenyl groups from allyl to octenyl). Especially preferred are methyl or ethyl since there are a number of commercially available alkylating agents which are especially suitable for the preparation of the methyl and ethyl analogs.

The anion $A^-$ may be any suitable anion, its sole purpose being to neutralize the charge of the anion, i.e. as a gegen ion. This function could be satisfied by any negatively charged species which would not react with and alter the cation. For example, simple anions such as choride, bromide, iodide, sulfate, phosphate, carbonate etc. would be suitable.

As a practical matter, however, the anion is normally determined by the alkylating agent used. The most reactive alkylating agents such as dimethyl sulfate, diethyl sulfate, methyl fluorosulfonate, trimethyloxonium fluoroborate, triethyloxonium fluoroborate, trimethyloxonium hexachloroantimonate, n-propyl or n-octyl trifluoromethane sulfonate, trimethyloxonium hexafluorophosphate, methyl trifluoromethane sulfonate, allyl trifluoromethanesulfonate, etc. are preferred, and these provide salts having anions such as fluorosulfonate, methylsulfate, ethylsulfate, trifluoromethanesulfonate, hexachloroantimonate, hexafluorophosphate, tetrafluoroborate, etc. respectively.

The 2-alkyl-3-haloisothiazolium salts of this invention are prepared by quaternization of the corresponding 3-haloisothiazole with a suitable alkylating agent. It is preferred to use the most reactive alkylating agents such as dimethyl sulfate, diethyl sulfate, methyl fluorosulfonate, trimethyloxonium fluoroborate, triethyloxonium fluoroborate, trimethyloxonium hexachloroantimonate, n-propyl or n-octyl trifluoromethane sulfonate, trimethyloxonium hexafluorophosphate, methyl trifluoromethane sulfonate, allyl trifluoromethanesulfonate, and the like. Especially preferred are the commercially available agents such as dimethyl sulfate, diethyl sulfate, methyl fluorosulfate, methyl fluorosulfonate, trimethyloxonium fluoroborate, triethyloxonium fluoroborate and the like. Such reagents, known in the art, are preferred since reactions utilizing them occur more rapidly and under milder reaction conditions than those using less reactive alkylating agents such as alkyl halides.

In the preferred process of this invention, the appropriate alkylating agent and isothiazole are brought together and heated to a reaction temperature that is sufficient to effect reaction. The relative amounts of the reactants are not critical and while equimolar amounts are normally preferred, an excess of either reagent is suitable. It is preferred to run the reaction without solvent, but a suitable reaction inert solvent may be used if desired. (The choice of solvent is within the skill of the art, typical examples being methylene chloride, chloroform, ethylene dichloride, ethers such as ethyl ether, dibutyl ether, diphenyl ether, etc.)

The reaction temperature preferred varies with the relative reactivities of the reagents. They normally do not exceed reflux temperature of the reaction mixture. If the reaction temperature required exceeds the boiling point of the reaction mixture, or one of its components, it may be necessary to achieve a higher temperature by running the reaction under pressure in a sealed reaction vessel.

The maximum temperature need only be kept below the thermal decomposition point of the reactants and product involved. Normally, temperatures are not lower than 0° C. nor higher than 250° C. When the more active alkylating agents are used, the preferred range is from about 25° C. to 150° C.

Parameters such as the temperature, reaction time etc. depend upon the relative reactivity of the specific reactants used. The reaction may be complete in as short a time as two minutes, or require as long as forty eight hours.

The salts produced can be purified if necessary by means known in the art. It is usually sufficient to merely wash out excess starting materials with an appropriate solvent such as toluene, benzene, ether, etc. and the like. If further purification is required the salts may be recrystallized from a suitable solvent.

As mentioned, the nature of the anion is immaterial for the applications of this invention with the possible exception certain special applications. If, for any reason, an anion is desired which differs from that normally determined by the alkylating agent, a simple exchange reaction can be run as illustrated below

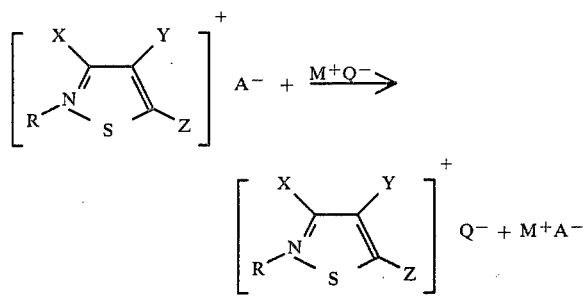

Such an exchange is most thoroughly and efficiently accomplished when $M^+$ is the cationic portion of an ion exchange resin or $M^+$ is chosen such that $M^+A^-$ will precipitate from the solution while the resulting 2-alkyl-3-haloisothiazolium salt will remain in solution. In the examples there is provided an illustration wherein such an exchange is carried out using silver nitrate as $M^+Q^-$. In that case silver fluorosulfonate precipitated while the isothiazolium nitrate remained in solution.

While it is preferred to choose $M^+Q^-$ so that either $M^+A^-$ or the new isothiazolium salt produced will precipitate out of solution, the exchange could be effected by creating an equilibrium, removing the solvent and separating the salts by methods known in the art, for example recrystallization techniques. Quite obviously, mixtures of salts wherein the anions are different would also be suitable since such mixtures would have the desired chemical and antimicrobial properties.

The number of inorganic or organic salts that could be used in such an exchange are countless, and it is expected that a chemist skilled in the art could choose a suitable reagent from among these. Such a chemist should, of course, avoid reagents which could be expected to react with the cation, for example an alkali hydroxide, an alkali sulfide etc. Such exchange reactions are, insofar as is pertinent to this invention, merely illustrative of the ease with which a different anion may be introduced if desirable for any reason.

As mentioned, the novel 2-alkyl-3-haloisothiazolium salts of this invention have two major uses. In addition to being useful in a variety of media to inhibit growth of bacteria and fungi, they may be used as intermediates to prepare other antimicrobial agents such as 2-alkyl-3-dicyanomethylene-4-isothiazolines, 2-alkyl-4-isothiazolin-3-thiones and 2-alkyl-4-isothiazolin-3-ones.

The 2-alkyl-3-dicyanomethylene-4-isothiazolines are prepared as illustrated below:

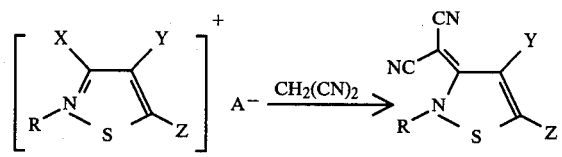

The groups R, X, Y, Z and A are as previously defined.

The conversion is very facile. It is preferred to simply mix the malononitrile with the 2-alkyl-3-halothiazolium salt in the presence of a suitable polar solvent. As the product is formed it usually precipitates from the reaction solvent and is isolated by methods commonly employed in the art.

Neither temperature nor time is critical. For convenience it is preferred to run the reaction at room temperature, but reaction temperatures from below 0° C. to above 100° C. would be suitable.

The reaction time may vary from 2 min. to 12 hrs. and would, of course, depend on the temperature.

Any solvent capable of solubilizing the salts such as ethanol, methanol, acetonitrile, and the like would be suitable.

As illustrated below, the 2-alkyl-3-haloisothiazolium salts provide a convenient starting material for the novel 2-alkyl-4-isothiazolin-3-thiones.

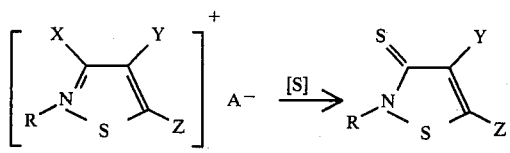

The suitable source of sulfur, [S], may be provided by a number of reactants such as thiourea, sodium sulfide, sodium hydrosulfide, methyl mercaptan, ethyl xanthate including analogs of the above such as potassium sulfide, lithium sulfide, hydrogen sulfide, methyl through octyl mercaptans, methyl through octyl xanthates, methyl through octyl thioureas and the like.

Again, the conversion is very facile. In the especially preferred process, it is simply necessary to mix thiourea with the 2-alkyl-3-haloisothiazolium salt in the presence of a suitable polar solvent. As the product is formed it normally precipitates from the reaction medium and can be collected by filtration.

Neither temperature nor time is critical. For convenience it is preferred to carry out the reaction at room temperature, but reaction temperatures from below 0° C. to above 100° C. would be suitable.

The reaction time may vary from 30 min. to 12 hrs. and would, of course, depend on the temperature.

The nature of the solvent is not critical and solvents capable of dissolving the salt such as methanol, ethanol, acetonitrile and the like are suitable.

Similarly the 3-halo-2-alkylisothiazolium salts of the invention can be reacted with a suitable oxygen source to provide 2-alkyl-4-isothiazolin-3-ones as shown below.

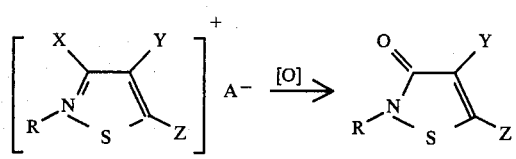

The reaction mechanism for the conversion of the 2-alkyl-3-haloisothiazolium salts is not clear. It would appear that a number of oxygen sources such as urea, amides (e.g. acetamide, formamide, dimethylacetamide, dimethylformamide) alcohols (e.g. methanol, ethanol, propanol, butanol), water, sulfoxides (e.g. dimethyl sulfoxide) and the like would be suitable. Of course, since it is the oxygen functionality of the above that is the "source of oxygen" and not the length or nature of the side chain, the higher analogs of the above should also be suitable. It has even been found that the anionic portion of the salt can be a suitable oxygen source as illustrated below.

Clearly, water is the preferred reagent since the salts are soluble in the reaction medium and the product normally precipitates as formed. Since a halogen acid is the expected byproduct, it is especially preferred to run the reaction in the presence of a base which neutralizes the acid formed. Any base capable of neutralizing the acid formed would be suitable. Preferred are the commonly available carbonates, bicarbonates, salts of organic acids such as acetates, and hydroxides.

Again, the conversion is very facile. In an especially preferred process the 2-alkyl-3-haloisothiazolium salt of this invention is added to a sodium acetate solution. As the product is formed it normally precipitates from the reaction medium and can be collected by filtration.

Neither temperature nor time appears to be critical, for convenience it is preferred to carry out the reaction at room temperature, but reaction temperatures from below 0° C. to above 100° C. would be suitable.

The reaction time may vary from a few minutes to 12 hrs. and would, of course, be dependent on the temperature.

An alternative method of synthesis is available when the anion is a suitable oxygenated species, e.g. a sulfate derivative such as methyl sulfate. In such cases the 2-alkyl-3-haloisothiazolium salt may be pyrolysed to yield the desired 2-alkyl-4-isothiazolin-3-one as illustrated below. The pyrolysis temperature may vary from 150° C. to 300° C. with 160° C. to 220° C. being especially

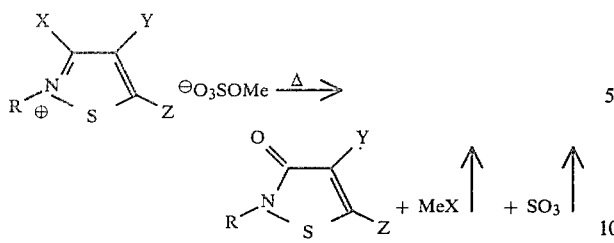

preferred.

It should be noted that while ethanol, reacts with the 2-alkyl-3-haloisothiazolium salt to convert it to 2-alkyl-4-isothiazolin-3-one, ethanol can be used as the solvent when the salt is reacted with thiourea to form the corresponding 2-alkyl-4-isothiazolin-3-thione. Apparently the thiourea reacts more rapidly than the ethanol.

It is difficult to determine in a reaction with both urea and ethanol present, just where the oxygen comes from which forms the carbonyl group of the 2-alkyl-4-isothiazolin-3-one produced. It is sufficient to note that the 2-alkyl-3-halo-isothiazolium salts of this invention are very reactive and are capable of reacting with a number of oxygen bearing reagents to form 2-alkyl-4-isothiazolin-3ones.

As mentioned, the novel 2-alkyl-3-haloisothiazolium salts, I, the novel 2-alkyl-4-isothiazolin-3thiones, III, and 2-alkyl-3-dicyanomethylene-4-isothiazolines, IV, are effective antibacterial and antifungal agents. These novel compounds (i.e. I, III and IV) may be added to such aqueous systems or formulations that are susceptible to acterial or fungal growth, either undiluted or dissolved in organic solvents such as alcohols, acetone, dimethylformamide and the like. They may be added alone or in combination with other biocides and/or functional compounds such as antioxidants, anticorrosive agents, surfactants, etc.

Concentrations from about 0.001% to above 1.0% are effective. Use of larger concentrations, while feasible, is recommended only for unusual applications. It is preferred to use concentrations from about 0.005% to about 0.5%.

The novel compounds I, III and IV may also be used as preservatives for oil in water emulsions. A number of oil in water emulsions are used in industry, for example in the high speed metal working and textile industries, for their cooling, lubricating, antistatic and anticorrosive properties. Unless adequately protected by an effective preservative, such systems are susceptible to bacterial decomposition producing obnoxious odors and potential health hazards. [Detailed descriptions of these systems, their microbiological problems and difficulties in their preservation can be found in: Bennet, E. O. Soap Chem. Specialties, 32, 46 (1956). Fabian, F. W. & Pivnick, H., Applied Microbiology, 1, (1953).]

In practicing the invention, the compound may be added by directly dissolving it in the concentrated oil which is then diluted with water to form the water oil emulsion, or it may be added to the final emulsion either undiluted or dissolved in a solvent such as dimethylformamide, alcohol, acetone, etc. Similar methods known in the art for adding preservatives to such water and oil emulsions may also be used.

There can be used as little as about 0.005%. Although amounts greater than 0.3% are operable, they are recommended only for unusual applications. It is preferred to use amounts in the range of from about 0.01% to about 0.20%, with amounts in the range of about 0.02% to 0.10% being especially preferred.

The novel compounds I, III and IV may also be used as cosmetic preservatives [Problems encountered in the preservation of cosmetics are described by Dunnigan, A.P., Drug and Cosmetic Industries, 103, 43, (1968)].

The compounds may be added to the finished cosmetic product directly or dissolved in suitable solvents such as alcohol, acetone, dimethyl formamide and the like. Alternatively the compounds may be dissolved in the oils or other raw materials used in the formula and then formulated in the final product.

In cosmetic preparations, concentrations as low as 0.01% are found to be operable. Concentrations greater than 0.30%, while operable, are recommended only for unusual applications. Concentrations in the range of from about 0.02% to about 0.20% are preferred with concentrations of about 0.05% to 0.10% being especially preferred.

The novel compounds I, III and IV are particularly effective as slimicides. For example they can be used to protect so-called white water systems utilized in paper manufacture from the formation of slimes and the like which are known to affect these systems. Concentration as low as 0.001% are found to be operable. Concentrations greater than 0.20%, while operable, are recommended only for unusual applications. Concentrations in the range of from about 0.002% to about 0.1% are preferred with concentrations of about 0.005 to about 0.01% being especially preferred.

While the compound is effective when added directly, it is preferred to add it dissolved in a suitable solvent such as diethylene glycol, dipropylene glycol or polyethylene glycol and the like. Other methods known in the art for adding preservatives to such aqueous systems may also be used.

The novel compounds I, III and IV are also effective preservatives of latex paints. They may be incorporated into the paint in a variety of ways. It is expected that those skilled in the art would determine the preferred method of introducing it in the paint. Among the methods available are introducing the fungicide as the paint is blended, mulling the fungicide into the paint, introducing a solution of the fungicide into the paint etc.

Normally the concentration of the compounds in the paint will be less than 1.0%. Higher amounts, though operable, would not be economical.

An amount of the novel compound at a concentration level of 0.1% to 1.0% in the liquid paint would suffice for most purposes. A concentration of about 0.2% to 0.7% is preferred for most applications, with about 0.5% being especially preferred.

ILLUSTRATION OF PREFERRED EMBODIMENTS

A number of examples are provided herein to illustrate the preferred embodiments of this invention. Included are examples directed to the synthesis of the novel compounds of this invention and examples directed to the utility of these compounds.

The examples provided herein are included for the sole purpose of illustrating the preferred embodiments and should not be construed as limiting. They are intended to embrace any equivalents or obvious extensions which are known or should be known to a person skilled in the art.

Synthesis of the 2-Alkyl-3-haloisothiazolium Salts

The following examples illustrate the method of synthesis of the 2-alkyl-3-haloisothiazolium salts of this invention.

EXAMPLE I

A. 2-Methyl-3,4,5-trichloroisothiazolium fluorosulfonate

Trichloroisothiazole (37.7 g, 0.20 mol) and 38 ml of methyl fluorosulfonate were mixed under a nitrogen atmosphere. The mixture was heated at 70°–80° for 30 min. The resulting solid was washed with ether and benzene to yield 55.6 g (96%) of 2-methyl-3,4,5-trichloroisothiazolium fluorosulfonate, mp 162 (d). Analysis-calculated for $C_4H_3Cl_3FNO_3S_2$: C, 15.87; H, 0.99; N, 4.63; Found: C, 15.81; H, 1.02; N, 4.49.

B. 2-Methyl-3,4,5-trichloroisothiazolium methylsulfate

Trichloroisothiazole (37.7 g, 0.20 mol) and dimethyl sulfate (9.5 ml, 0.1 mol) were mixed under a nitrogen atmosphere. The mixture was heated at 135°–140° for 1 hr. The reaction mixture was cooled and poured into 100 ml of ether. The resulting solid was collected and washed with warm glyme to yield 14.5 g, (46%), mp 130°. The NMR and IR were consistent with the assigned structure.

C. 2-Methyl-3,4,5-trichloroisothiazolium hexafluorophosphate

Trichloroisothiazole (15 ml) and 6.2 g (0.03 mol) of trimethyloxomium hexafluorophosphate were heated at 90° for 1 hr. under nitrogen. After cooling, either (b 100 ml) was added and the solid collected to yield 6.3 g (61%) of product, mp>240. Spectral data (NMR & IR) were consistent with the assigned structure.

D. 2-Methyl-3,4,5-trichloroisothiazolium trifluoromethane sulfonate

Trichloroisothiazole (9.4 g, 0.05 mol) and 9 ml of methyl trifluoromethane sulfonate were heated at 65° for 30 min. After cooling, either (150 ml) was added and the solid collected to yield 4.6 g (26%) of product, mp 118–120. Spectral data (NMR & IR) were consistent with the assigned structure.

E. 2-Methyl-3,4,5-trichloroisothiazolium hexachloroantimonate

Trichloroisothiazole (10 ml) and trimethyloxonium hexachloroantimonate (7.9 g, 0.02 mol) were heated at 90° for 30 min. After cooling either (150 ml) was added and the solid collected to yield 7.8 g (73%) of product, mp >240. Spectral data (NMR & IR) were consistent with the assigned structure.

F. 2-Methyl-3,4,5-tribromoisothiazolium fluorosulfonate

Tribromoisothiazole (2.2 g, 0.007 mol) and 2.2 ml of methyl fluorosulfonate were heated at 65° for 10 min. under a nitrogen atmosphere. The resulting solid was washed with ether and benzene to yield 2.7 g. (88%) of 2-methyl-3,4,5-tribromoisothiazolium fluorosulfonate, mp 121–129. Spectral data (NMR and IR) were consistent with the assigned structure.

G. 3,4-Dichloro-2,5-dimethylisothiazolium fluorosulfonate 3,4-Dichloro-4-methylisothiazole (6.5 g, 0.039 mol) and 7 ml of methyl fluorosulfonate were heated at 70° for 30 min. under a nitrogen atmosphere. The resulting solid was washed with ether and benzene to yield 10.1 g (92%) of 3,4-dichloro-2,5-dimethylisothiazolium fluorosulfonate, mp 152–162. Analysis - calculated for $C_5H_6Cl_2FNO_3S_2$: C, 21.28; H, 2.14; Cl, 25.13; N, 4.97; S, 22.73. Found: C, 21.22; H, 2.19; Cl, 25.01; N, 5.18; S, 22.74.

H. 4-Cyano-3,5-dichloro-2-methylisothiazolium fluorosulfonate

4-Cyano-3,5-dichloroisothiazole (5.0 g, 0.028 mol) and 4 ml of methyl fluorosulfonate were heated at 80°–90° for 30 min under a nitrogen atmosphere. The resulting solid was washed with ether and benzene to yield 7.5 g (92%) of 4-cyano-3,5-dichloro-2-methyl-isothiazolium fluorosulfonate, mp 160–170. Spectral data (NMR and IR) were consistent with the assigned structure. Analysis-calculated for $C_5H_3Cl_2FN_2O_3S_2$: C, 20.50; H, 1.02; Found: C,20.27;H, 1.44.

I. 5-Cyano-3,4-dichloro-2-methylisothiazolium fluorosulfonate

5-Cyano-3,4-dichloroisothiazole (3.6 g, 0.02 mol) and 4 ml of methyl fluorosulfonate were heated at 80°–100° for 1½ hrs under a nitrogen atmosphere. The resulting solid was washed with ether and benzene to yield 4.5 g (77%) of 5-cyano-3,4-dichloro-2-methyl isothiazolium fluorosulfonate, mp 163–174 (d). Spectral data (NMR and IR) were consistent with the assigned structure.

J. 3,4-Dichloro-2-methyl-5-ethoxycarbonylisothiazolium fluorosulfonate 3,4-Dichloro-5-ethoxycarbonylisothiazole (6.0 g, 0.027 mol) and 4 ml of methyl fluorosulfonate were heated at 110° for 1 hr under a nitrogen atmosphere. The solid was washed with ether and benzene to yield 9.0 g (99%) of 3,4-dichloro-2-methyl-5-ethoxycarbonylisothiazolium fluorosulfonate, mp 118–123. Analysis-calculated for $C_7H_8Cl_2FNO_5S_2$: Cl, 20.84; N 4.12; S, 18.85. Found Cl, 20.56; N, 4.06; S, 18.89.

K. 3,4-Dichloro-2-methylisothiazolium fluorosulfonate 3,4-Dichloroisothiazole (3.1 g, 0.02 mol) and 4 ml of methyl fluorosulfonate were heated at 40° for 15 min under a nitrogen atmosphere. The resulting solid was washed with ether and benzene to yield 3.4 g (63%) of 3,4-dichloro-2-methylisothiazolium fluorosulfonate, mp 159–164. Analysis-calculated for $C_4H_4Cl_2FNO_3S_2$: C, 17.90; H, 1.49; Cl, 26.45; F, 7.90; N, 5.22. Found C, 17.74; H, 1.49; Cl, 26.49; F, 7.24; N, 5.13.

L. 2-Propyl-3,4,5-trichloroisothiazolium trifluoromethane sulfonate

Trichloroisothiazole (4.7 g, 0.025 mol) and a solution of 0.02 mol of n-propyl trifluoromethane sulfonate in $CCl_4$ were heated at 110° and $CCl_4$ was removed via distillation. After heating at 110° for 1½ hrs, the reaction was cooled and ether added. The ether was cooled in an ice bath and the solid collected to yield 2.1 g (28%) of product, mp 95°–99°. Analysis calculated for $C_7H_7Cl_3F_3NO_3S$: C, 22.09; H, 1.86; Cl, 27.95; N, 3.68;

S, 16.84. Found: C, 2160; H, 1.94; Cl, 27.15; N, 3.57; S, 16.27.

M. 2-Octyl-3,4,5-trichloroisothiazolium trifluoromethane sulfonate

Trichloroisothiazole (6.6 g, 0.035 mol) and n-octyl trifluoromethane sulfonate (7.5 g, 0.0286 mol) were heated at 110° for 2 hrs. After cooling, 150 ml of ether was added and solution cooled in dry ice/acetone bath. The ether was decanted and the brown oil dried to yield 4.0 g (31%) of product. Spectral data (NMR & IR) were consistent with the assigned structure.

N. 2-(2-Propen-1-yl)-3,4,5-trichloroisothiazolium trifluoromethane sulfonate Trichloroisothiazole (5.7 g, 0.03 ml) and a solution of allyl trifluoromethane sulfonate (0.03 mol) in CCl$_4$ were heated and excess CCl$_4$ was removed by distillation until the reacting temperature reached 90° C. After heating at 90° for 30 min, the reaction was cooled and 150 ml of ether added. The solid was collected to yield 2.6 g (30%) of product, mp 103–105. Spectral data (NMR & IR) were consistent with the assigned structure.

O. 2-Ethyl-3,4,5-trichloroisothiazolium tetrafluoroborate

Trichloroisothiazole (37.7 g, 0.20 mol) and triethyloxonium fluoroborate (19.0 g, 0.10 mol) were heated at 110° for 1 hr under a nitrogen atmosphere. The resulting solid was washed with ether to yield 15.1 g (50%) of 2-ethyl-3,4,5-trichloroisothiazolium, tetrafluoroborate mp 193–197. Analysis-calculated for C$_5$H$_5$BCl$_3$F$_4$NS: C, 19.74; H, 1.64; Cl, 34.95; N, 4.59; S, 1054. Found: C, 19.88; H, 1.70; Cl, 35.05; N, 4.58; S, 10.91.

P. 2-Methyl-3-chloroisothiazolium nitrate

3-Chloroisothiazolium fluorosulfonate (6.9, 0.03) and 5.1 g of AgNO$_3$ were dissolved in 280 ml of acetonitrile. After stirring for 30 min, the AgOSO$_2$F was removed by filtration and the acetonitrile concentrated on the rotary evaporator. THF was added and the solid collected to yield 5.8 g (98%) of product, mp 175 (d). Spectral data (NMR & IR) were consistent with assigned structure.

Q. Other 2-alkyl-3-haloisothiazolium salts

A number of other 2-alkyl-3-haloisothiazolium salts were prepared in a similar manner and are listed in Table I, Example II.

ILLUSTRATION OF GENERAL ANTIMICROBIAL ACTIVITY

EXAMPLE II

2-Alkyl-3-chloroisothiazolium salts

Antibacterial and antifungal activity were evaluated by a 5-fold serial dilution test in agar. In this test, compounds were prepared as 6% solutions in dimethylformamide or ethanol. The 6% solution was then 5-fold serially diluted in test tubes to give the desired concentrations when mixed with agar and poured into sterile Petri dishes. Tryptone glucose extract agar was used for the bacterial testing; mildew glucose agar for the fungal testing. The bacterial plates were spot inoculated with 24-hour nutrient broth cultures and incubated at 37° C. for 48 hours. The fungal plates were spot inoculated with spore suspensions and incubated at 28° C. for seven days. At the end of the incubation periods, all plates were examined for growth. The minimum inhibitory concentration (MIC) for each organism is expressed in Table I. In the ranges presented, growth is observed only in the lower concentration. The key to Table I is as follows:

| Activity | Growth @ | | No Growth @ | |
|---|---|---|---|---|
| 0 | >1920 | μg/ml | | |
| 1 | 384 | μg/ml | 1920 | μg/ml |
| 2 | 76 | μg/ml | 384 | μg/ml |
| 3 | 15 | μg/ml | 76 | μg/ml |
| 4 | 3 | μg/ml | 15 | μg/ml |
| 5 | 0.6 | μg/ml | 3 | μg/ml |
| 6 | 0.12 | μg/ml | 0.6 | μg/ml |
| 7 | .03 | μg/ml | .12 | μg/ml |
| 8 | | | <.03 | μg/ml |

The organisms tested are:

| Bacteria | | Fungi | |
|---|---|---|---|
| B$_1$ | S. aureus | F$_1$ | A. niger |
| B$_2$ | E. coli | F$_2$ | A. oryzae |
| B$_3$ | P. aeruginosa | F$_3$ | P. piscarium |
| B$_4$ | P. vulgaris | F$_4$ | A. pullulans |
| B$_5$ | B. subtilis | | |

TABLE I

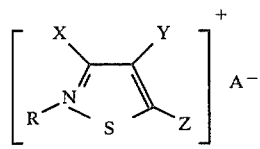

| No. | Cation R | X | Y | Z | Anion A$^-$ | Melting Point °C. | Bacteria B$_1$ | B$_2$ | B$_3$ | B$_4$ | B$_5$ | Fungi F$_1$ | F$_2$ | F$_3$ | F$_4$ |
|---|---|---|---|---|---|---|---|---|---|---|---|---|---|---|---|
| 1 | CH$_3$ | Cl | Cl | Cl | $^-$O$_3$SF | 162 (d) | 6 | 6 | 5 | 6 | 6 | 8 | 8 | 8 | 8 |
| 2 | CH$_3$ | Cl | Cl | Cl | $^-$O$_3$SOMe | 135–140 | 5 | 5 | 4 | 5 | 5 | 8 | 8 | 8 | 8 |
| 3 | CH$_3$ | Cl | Cl | Cl | $^-$SbCl$_6$ | >240 | 4 | 5 | 4 | 5 | 5 | 6 | 6 | 7 | 7 |
| 4 | CH$_3$ | Cl | Cl | Cl | $^-$O$_3$SCF$_3$ | 118–20 | 5 | 5 | 4 | 5 | 5 | 7 | 7 | 7 | 8 |
| 5 | CH$_3$ | Cl | Cl | Cl | $^-$PF$_6$ | >240 | 4 | 3 | 3 | 4 | 5 | 6 | 6 | 5 | 7 |
| 6 | CH$_3$ | Br | Br | Br | $^-$O$_3$SF | 121–9 (d) | 4 | 3 | 3 | 4 | 5 | 6 | 6 | 5 | 7 |
| 7 | Ethyl | Cl | Cl | Cl | $^-$BF$_4$ | 193–7 | 6 | 5 | 3 | 6 | 6 | 8 | 8 | 8 | 8 |
| 8 | Ethyl | Cl | Cl | Cl | $^-$O$_3$SF | 124–7 | | | | | | | | | |
| 9 | Ethyl | Cl | Cl | Cl | $^-$O$_3$SOEt | liquid | | | | | | | | | |
| 10 | Propyl | Cl | Cl | Cl | $^-$O$_3$SCF$_3$ | 95–9 | 5 | 5 | 3 | 5 | 5 | 7 | 7 | 7 | 8 |

TABLE I-continued $$\left[\begin{array}{c} X \quad Y \\ \| \quad \| \\ R^{N} \diagdown_{S} \diagup^{Z} \end{array}\right]^{+} A^{-}$$

| No. | Cation R | X | Y | Z | Anion $A^-$ | Melting Point °C. | Bacteria $B_1$ | $B_2$ | $B_3$ | $B_4$ | $B_5$ | Fungi $F_1$ | $F_2$ | $F_3$ | $F_4$ |
|---|---|---|---|---|---|---|---|---|---|---|---|---|---|---|---|
| 11 | Allyl | Cl | Cl | Cl | $^-O_3SCF_3$ | 103-5 | 4 | 4 | 3 | 4 | 4 | 7 | 7 | 8 | 7 |
| 12 | Octyl | Cl | Cl | Cl | $^-O_3SCF_3$ | liquid | 4 | 4 | 3 | 4 | 5 | 8 | 7 | 7 | 7 |
| 13 | $CH_3$ | Cl | H | H | $^-O_3SCF$ | 215-26 | 2 | 3 | 3 | 4 | 4 | 2 | 2 | 3 | 3 |
| 14 | $CH_3$ | Cl | H | H | $^-O_3SOMe$ | 100-3 | 2 | 3 | 3 | 3 | 3 | 3 | 1 | 2 | 2 |
| 15 | $CH_3$ | Cl | H | H | $^-NO_3$ | 175 (d) | 3 | 3 | 3 | 3 | 3 | 4 | 4 | 5 | 3 |
| 16 | $CH_3$ | Cl | H | H | $^-SbCl_6$ | >240 | 2 | 2 | 3 | 3 | 3 | 3 | 3 | 3 | 3 |
| 17 | $CH_3$ | Cl | H | H | $^-PF_6$ | >240 | 2 | 3 | 3 | 3 | 3 | 1 | 1 | 2 | 2 |
| 18 | Ethyl | Cl | H | H | $^-O_3SOEt$ | liquid | 2 | 3 | 2 | 3 | 2 | 1 | 1 | 2 | 2 |
| 19 | Ethyl | Cl | H | H | $^-O_3SF$ | 81-3 | 2 | 3 | 3 | 3 | 3 | 3 | 3 | 3 | 4 |
| 20 | Propyl | Cl | H | H | $^-O_3SCF_3$ | 50-3 | 2 | 3 | 2 | 3 | 3 | 3 | 2 | 3 | 3 |
| 21 | Octyl | Cl | H | H | $^-O_3SCF_3$ | liquid | 3 | 3 | 1 | 3 | 4 | 5 | 5 | 5 | 6 |
| 22 | $CH_3$ | Cl | Cl | H | $^-O_3SF$ | 159-64 | 4 | 4 | 3 | 4 | 4 | 1 | 2 | 2 | 2 |
| 23 | $CH_3$ | Cl | Cl | H | $^-O_3SOMe$ | 81-85 | 4 | 4 | 3 | 5 | 5 | 2 | 2 | 2 | 2 |
| 24 | $CH_3$ | Cl | Cl | COOEt | $^-O_3SF$ | 107-110 | 3 | 3 | 2 | 4 | 4 | 2 | 2 | 2 | 2 |
| 25 | $CH_3$ | Cl | Cl | C≡N | $^-O_3SF$ | 167-74 | 3 | 3 | 2 | 4 | 4 | 3 | 2 | 2 | 2 |
| 26 | $CH_3$ | Cl | C≡N | Cl | $^-O_3SF$ | 160 (d) | 4 | 4 | 3 | 4 | 4 | 4 | 4 | 4 | 5 |
| 27 | $CH_3$ | Cl | Cl | $CH_3$ | $^-O_3SF$ | 155 | 2 | 2 | 1 | 2 | 2 | 3 | 3 | 3 | 3 |
| 28 | $CH_3$ | Cl | $NO_2$ | H | $^-O_3SF$ | 145-150 | 1 | 1 | 1 | 2 | 2 | 1 | 1 | 2 | 3 |

Illustration of Specific Applications microorganisms and then reinoculated and incubated. Results are tabulated in Table II.

TABLE II $$\left[\begin{array}{c} X \quad Y \\ \| \quad \| \\ R^{N} \diagdown_{S} \diagup^{Z} \end{array}\right]^{+} A^{-}$$

MINIMUM INHIBITORY CONCENTRATION (μg/ml)

| Cation R | X | Y | Z | Anion $A^-$ | Incubation Period (Weeks) 1 | 2 | 3 | 4 |
|---|---|---|---|---|---|---|---|---|
| $CH_3$ | Cl | Cl | Cl | $^-O_3SF$ | <16 | <16 | <16 | <16 |
| $CH_3$ | Cl | Cl | Cl | $^-O_3SOMe$ | <2 | <2 | <16 | <16 |
| $CH_3$ | Cl | Cl | Cl | $^-SbCl_6$ | 2 | 2 | 2 | 64 |
| $CH_3$ | Cl | Cl | Cl | $^-O_3SCF_3$ | 2 | 2 | 16 | 64 |
| Ethyl | Cl | Cl | Cl | $^-BF_4$ | 4 | 8 | 8 | 32 |
| Propyl | Cl | Cl | Cl | $^-O_3SCF_3$ | <32 | <32 | <32 | <32 |
| $CH_3$ | Cl | H | H | $^-O_3SF$ | 32 | 32 | 32 | 32 |
| $CH_3$ | Cl | H | H | $^-O_3SOMe$ | 64 | 64 | 64 | 64 |
| $CH_3$ | Cl | H | H | $^-NO_3$ | 8 | 8 | 8 | 8 |
| $CH_3$ | Cl | H | H | $^-SbCl_6$ | 8 | 16 | 16 | 16 |
| $CH_3$ | Cl | H | H | $^-PF_6$ | 32 | 32 | 32 | 32 |
| Ethyl | Cl | H | H | $^-O_3SOEt$ | 125 | 125 | 125 | 500 |
| Propyl | Cl | H | H | $^-O_3SCF_3$ | 125 | 250 | 250 | 500 |
| $CH_3$ | Cl | Cl | H | $^-O_3SF$ | 32 | 32 | 125 | 250 |
| $CH_3$ | Cl | Cl | H | $^-O_3SOMe$ | 32 | 32 | 32 | 32 |
| $CH_3$ | Cl | Cl | COOEt | $^-O_3SF$ | 125 | 250 | 250 | 250 |
| $CH_3$ | Cl | Cl | C≡N | $^-O_3SF$ | <16 | 125 | 250 | 250 |
| $CH_3$ | Cl | C≡N | Cl | $^-O_3SF$ | <16 | 125 | 250 | 250 |
| $CH_3$ | Cl | Cl | $CH_3$ | $^-O_3SF$ | 125 | 250 | 500 | 500 |
| $CH_3$ | Cl | $NO_2$ | H | $^-O_3SF$ | 125 | 500 | 500 | 500 |

EXAMPLE III

The efficacy of 2-alkyl-3-haloisothiazolium salts as a preservative for cutting oil emulsions was demonstrated by the following test:

Various aliquots of a 6% solution of the chemical in ethanol were added to cutting oil emulsions prepared by diluting Kutwell 30 cutting oil concentrate 1 to 30 with water. These samples were inoculated with a culture of Ps. aeruginosa and incubated at 28° on a rotary shaker. At weekly intervals the samples were examined for

EXAMPLE IV

The efficacy of 2-alkyl-3-haloisothiazolium salts as a preservative for latex paints was demonstrated by the following test.

Various quantities of the chemical were incorporated into a white exterior vinyl acetate paint. Whatman #30 filter paper was painted with one coat of paint on each side. One inch squares were cut and placed in Petri dishes on a malt agar.

The surface of both the agar and the painted squares were inoculated with a spore suspension of *Aureobasidium pullulans*. The plates were examined for zones of inhibition and surface growth after three weeks incubation in a humidity chamber at 27°–28°. The results are tabulated in Table III.

TABLE III $$\left[ \begin{array}{c} X \quad Y \\ \diagdown \; \diagup \\ \\ R-N \\ \diagdown_S \diagup_Z \end{array} \right]^+ A^-$$

| | | | | Conc. 0.5% *A. pullulans* | | Conc. 0.25% *A. pullulans* | |
|---|---|---|---|---|---|---|---|
| R | X | Y | Z | A⁻ | Zone Surface | Zone | Surface |
| CH₃ | Cl | Cl | Cl | −O₃SF | >20ᵃ Noneᵇ | 0 | None |
| CH₃ | Cl | Cl | Cl | −O₃SOMe | >20 None | 0 | None |
| CH₃ | Cl | CN | Cl | −O₃SF | 0 None | 0 | None |
| CH₃ | Cl | Cl | H | −O₃SF | 0 None | 0 | None |
| Et | Cl | Cl | Cl | −O₃SCF₃ | 20 None | 20 | None |
| CH₃ | Cl | Cl | Cl | −SbCl₆ | 20 None | 20 | None |
| Control | | | | | 0 Heavy | 0 | Heavy |

ᵃZone sizes are in mm.
ᵇGrowth on the surface on painted square: none, medium or heavy.

EXAMPLE V

The utility of the isothiazolium salts as a slimicide for pulp and paper mill water systems was demonstrated by the following study using 2-methyl-3,4,5-trichloroisothiazolium methyl sulfate.

Various quantities of a 6% solution of this compound in dimethylformamide were incorporated into 24 ml of a test substrate composed as follows:

8.4 g Whatman No. 2 cellulose
2.6 g Sodium nitrate
1.0 g Calcium sulfate
6.5 g Maltose
1.0 g Nutrient Broth, Difco
10.0 ml Mersize Rm 70R (Monsanto)
2.5 ml 2% Alum
990 ml Distilled Water The samples were inoculated with four different organisms and incubated at 28° C. At weekly intervals the samples were examined for the presence of microbial growth and reinoculated during a total incubation period of four weeks. The results as tabulated in Table IV show that 2-methyl-3,4,5-trichloroisothiazolium methyl sulfate is effective as a slimicide at a concentration of <0.01%.

TABLE IV

Effectiveness of 2-Methyl-3,4,5-Trichloroisothiazolium Methyl Sulfate As a Slimicide (mcg/ml)

| | Minimum inhibitory concentration (μg/ml) Weeks | | | |
|---|---|---|---|---|
| Organism | 1 | 2 | 3 | 4 |
| *P. aeruginosa* | 7.8 | 7.8 | 7.8 | 7.8 |
| *E. aerogenes* | 3.9 | 3.9 | 3.9 | 3.9 |
| *A. niger* | 3.9 | 3.9 | 3.9 | 3.9 |
| *P. Piscarium* | 3.9 | 3.9 | 3.9 | 3.9 |

Synthesis of 2-Alkyl-3-dicyanomethylene-4-isothiazolines

EXAMPLE VI

4-Chloro-3-dicyanomethylene-5-ethoxycarbonyl-2-methyl-4-isothiazoline 3,4-Dichloro-5-ethoxycarbonyl-2-methylisothiazolium fluorosulfonate (7.5 g, 0.022 mole) was dissolved in 75 ml of isopropanol. Malononitrile (1.5 g, 0.023 mol) was added the mixture stirred for 30 min. The yellow solid was collected and washed with isopropanol to yield 2.6 g (44%) of product, mp 134–136. Analysis calculated for $C_{10}H_8ClN_3O_2S_2$: C 44.51; H, 3.00; Cl, 13.16; N, 15.57; S, 11.90. Found: C, 44.34; H, 2.82; Cl, 12.60; N, 14.82; S, 11.42.

The other 2-alkyl-3-dicyanomethylene-4-isothiazolines can be prepared in a similar manner. A number of these are listed in Table V, Example VII.

Illustration of the General Antimicrobial Activity of the 2-Alkyl-3-dicyanomethylene-4-isothiazolines

EXAMPLE VII

The 2-alkyl-3-dicyanomethylene-4-isothiazolines were tested for antimicrobial activity as described in Example II. The results are listed in Table V. The key to the activity levels and the microorganisms used is as described in Example II.

TABLE V $$\begin{array}{c} NC \quad CN \\ \diagdown \; \diagup \\ C \\ \| \\ \diagup \quad \diagdown \quad Y \\ \\ R-N \\ \diagdown_S \diagup_Z \end{array}$$

| | | | Melting | Bacteria | | | | | Fungi | | | |
|---|---|---|---|---|---|---|---|---|---|---|---|---|
| R | Y | Z | Point | B₁ | B₂ | B₃ | B₄ | B₅ | F₁ | F₂ | F₃ | F₄ |
| CH₃ | Cl | Cl | 251 (d) | 4 | 3 | 2 | 3 | | 4 | 4 | 4 | 5 |
| CH₂CH₃ | Cl | Cl | 170–171 | 4 | 4 | 3 | 4 | 4 | 4 | 4 | 4 | 4 |
| CH₃ | H | H | 235–237 | 2 | 3 | 1 | 4 | 3 | 1 | 0 | 1 | 1 |
| CH₂CH₃ | H | H | 57–59 | 3 | 3 | 2 | 4 | 4 | 1 | 1 | 1 | 2 |
| CH₃ | Cl | H | 135 (d) | 3 | 4 | 3 | 4 | 4 | 1 | 1 | 1 | 2 |
| CH₃ | Cl | COOEt | 134–136 | 2 | 2 | 1 | 2 | 3 | 1 | 1 | 1 | 1 |
| CH₃ | Cl | CN | 190 (d) | 3 | 2 | 0 | 3 | 3 | 2 | 1 | 2 | 3 |
| CH₃ | Cl | CH₃ | 224–226 | 3 | 3 | 0 | 5 | 5 | 0 | 0 | 0 | 1 |

EXAMPLE VIII

The efficacy of 2-alkyl-3-dicyanomethylene-4-isothiazolines as a preservative for cutting oil emulsions was demonstrated by the test of Example III. Results are tabulated in Table VI.

TABLE VI

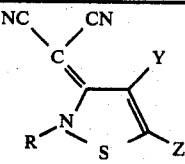

Minimum Inhibitory
Concentration (μg/ml)
Incubation Period (weeks)

| R | Y | Z | 1 | 2 | 3 | 4 |
|---|---|---|---|---|---|---|
| $CH_3$ | Cl | Cl | 125 | 125 | 250 | 250 |
| $C_2H_5$ | H | H | 125 | 250 | 250 | 500 |
| $CH_3$ | Cl | COOEt | 125 | 125 | 125 | 125 |
| $CH_3$ | Cl | CN | 62 | 250 | 250 | 250 |
| $CH_3$ | H | H | 250 | 500 | 500 | 500 |
| $CH_3$ | Cl | $CH_3$ | 250 | 500 | 500 | 1000 |
| $CH_3$ | Cl | H | <32 | <32 | <32 | <32 |

EXAMPLE IX

The test of Example V was used to determine the effectiveness of 4,5-dichloro-3-dicyanomethylene-2-methyl-4-isothiazoline as a slimicide. The results are tabulated in Table VII.

TABLE VII

| Organism | Minimum Inhibitory Concentration (μg/ml) Weeks | | | |
|---|---|---|---|---|
|  | 1 | 2 | 3 | 4 |
| P. aeruginosa | 250 | 250 | 250 | 250 |
| E. aerogenes | 250 | 250 | 250 | 250 |
| A. niger | 250 | 500 | 500 | 500 |
| P. Piscarium | 250 | 250 | 250 | 500 |

Synthesis of 2-Alkyl-4-isothiazolin-3-thiones

EXAMPLE X

A. 4,5-Dichloro-2-methyl-4-isothiazolin-3-thione

2-Methyl-3,4,5-trichloroisothiazolium methylsulfate (10.7 g) thiourea (2.6 g) were added to 100 ml of ethanol at room temperature. After stirring overnight the product which had precipitated from solution was collected by filtration and recrystallized from ethanol to yield 5.3 g (78%) of 4,5-dichloro-2-methyl-4-isothiazolin-3-thione, mp 143-144.

Analysis: Calculated for $C_4H_3ClNS_2$: C, 24.00; H, 1.50; N, 7.00; Cl, 35.45; S, 32.05. Found: C, 24.07; H, 1.45; N, 7.00; Cl, 35.67; S, 31.78.

Other 2-alkyl-4-isothiazolin-3-thiones can be prepared in a similar manner. A number of these are listed in Table VIII, Example XI.

EXAMPLE XI

The 2-alkyl-4-isothiazolin-3-thiones were tested for antimicrobial activity as described in Example II. The results are listed in Table VIII. The key to the activity levels and the microorganisms used is as described in Example II.

TABLE VIII

| No. | R | Y | Z | Melting Point | Bacteria | | | | | Fungi | | | |
|---|---|---|---|---|---|---|---|---|---|---|---|---|---|
|  |  |  |  |  | $B_1$ | $B_2$ | $B_3$ | $B_4$ | $B_5$ | $F_1$ | $F_2$ | $F_3$ | $F_4$ |
| 1 | $CH_3$ | Cl | Cl | 143-144 | 6 | 5 | 4 | 5 |  | 6 | 6 | 6 | 6 |
| 2 | $CH_2CH_3$ | Cl | Cl | 99-100 | 4 | 4 | 3 | 5 | 6 | 6 | 6 | 6 | 7 |
| 3 | $CH_3$ | H | H | 99-102 | 2 | 3 | 2 | 4 | 3 | 2 | 2 | 2 | 3 |
| 4 | $CH_3$ | Cl | H | 142 (d) | 3 | 4 | 2 | 4 | 4 | 4 | 3 | 6 | 5 |
| 5 | $CH_3$ | Cl | COOEt | 108-110 | 1 | 2 | 1 | 1 | 1 | 1 | 1 | 1 | 1 |
| 6 | $CH_3$ | Cl | CN | 211 (d) | 2 | 2 | 1 | 3 | 4 | 1 | 2 | 2 | 4 |
| 7 | $CH_3$ | Cl | $CH_3$ | 125-127 | 0 | 1 | 0 | 1 | 1 | 2 | 1 | 2 | 3 |

EXAMPLE XII

The efficacy of 2-alkyl-4-isothiazolin-3-thiones as a preservative for cutting oil emulsions was demonstrated by the test of Example III. The results are tabulated in Table IX.

TABLE IX

| R | Y | Z | Minimum Inhibitory Concentration (μg/ml) Incubation Period (weeks) | | | |
|---|---|---|---|---|---|---|
|  |  |  | 1 | 2 | 3 | 4 |
| $CH_3$ | Cl | Cl | <16 | 62 | 62 | 62 |
| $C_2H_5$ | Cl | Cl | 16 | 32 | 62 | 62 |
| $CH_3$ | H | H | 125 | 250 | 250 | 250 |
| $CH_3$ | Cl | H | <32 | 62 | 62 | 62 |
| $CH_3$ | Cl | COOEt | 250 | 125 | 125 | 62 |
| $CH_3$ | Cl | CN | 16 | 125 | 250 | 250 |

EXAMPLE XIII

Various quantities of 4,5-dichloro-2-methyl-4-isothiazolin-3-thione were incorporated into a white exterior vinyl acetate paint and tested as described in Example IV.

At both 0.5% and 0.25% the inhibiting zone was 20 mm and there was no growth on the surface.

EXAMPLE XIV

The utility of 2-alkyl-4-isothiazolin-3-thiones as a slimicide was tested as in Example V. The results are presented in Table X.

TABLE X

Effectiveness of 4,5-dichloro-2-methyl-4-isothiazolin-3-thione as a slimicide (mcg/ml).

| Organism | Minimum Inhibitory Concentration (μg/ml) Weeks | | | |
|---|---|---|---|---|
|  | 1 | 2 | 3 | 4 |
| P. aeruginosa | 16 | 16 | 16 | 16 |
| E. aerogenes | <8 | <8 | 16 | 16 |
| A. niger | <8 | <8 | <8 | <8 |

-continued

| Organism | Minimum Inhibitory Concentration (μg/ml) Weeks | | | |
|---|---|---|---|---|
| | 1 | 2 | 3 | 4 |
| P. piscarium | <8 | <8 | <8 | 16 |

Synthesis of 2-Alkyl-4-isothiazolin-3-ones From the Corresponding 2-Alkyl-3-halo-isothiazolium Salts The following examples illustrate the conversion of the 2-alkyl-3-halo-isothiazolium salts of this invention to the antimicrobially active 2-alkyl-4-isothiazolin-3-ones.

EXAMPLE XV 4,5-Dichloro-2-methyl-4-isothiazolin-3-one

2-Methyl-3,4,5-trichloroisothiazolium methylsulfate (15.5 g, 0.05 ml) was heated at 180°–190° until gas evolution ceased. The solid was recrystallized from chloroform to yield 4.6 g (50%) of 4,5-dichloro-2-methyl-4-isothiazolin-3-one, mp 117–120.

This example illustrates the method by which a 2-alkyl-3-halo-isothiazolium salt having a suitably oxygenated anion can be converted to the corresponding 2-alkyl-4-isothiazolin-3-one by pyrolysis.

EXAMPLE XVI

This example illustrates how the 2-alkyl-4-isothiazolin-3-ones can be prepared by reacting the corresponding 2-alkyl-3-haloisothiazolium salt with aqueous base.

A. 4,5-Dichloro-2-methyl-4-isothiazolin-3-one

2-Methyl-3,4,5-trichloroisothiazolium fluorosulfonate (16.9 g, 0.058 mol) was added in portions to 150 ml of a saturated sodium acetate solution. After stirring for 30 min. the solid was collected, washed with water, and recrystallized from ethanol to yield 7.5 g (70%) of 4,5-dichloro-2-methyl-4-isothiazolin-3-one, mp 119°–120°.

B. 4-Chloro-2-methyl-4-isothiazolin-3-one 3,4-Dichloro-2-methylisothiazolium fluorosulfonate (13.1 g, 0.049 mol) was added in portions to 150 ml of a saturated sodium acetate solution. After stirring for 30 min., the solid was collected and recrystallized from heptane to yield 5.2 g (70%) of 4-chloro-2-methyl-4-isothiazolin-3-one, mp 87°–90°.

Analysis: Calculated for $C_4H_4ClNOS$: C, 32.09; H, 2.67; Cl, 23.73; N, 9.36; S, 21.46. Found: C, 32.30; H, 2.72; Cl, 23.74; N, 9.11; S, 21.72.

C. 4-Chloro-5-ethoxycarbonyl-2-methyl-4-isothiazolin-3-one 3,4-Dichloro-5-ethoxycarbonyl-2-methylisothiazolium fluorosulfonate (4.2 g, 0.012 mol) was added to 50 ml of saturated $K_2CO_3$ solution. The aqueous phase was extracted with 3×50 ml of $CH_2Cl_2$. Then combined extracts were dried ($MgSO_4$), filtered and conc. to yield a solid. Recrystallization from heptane yielded 1.0 g (35%) of 4-chloro-5-ethoxycarbonyl-2-methyl-4-isothiazolin-3-one, mp 142–147.

Analysis: Calculated for $C_7H_8ClNO_3S$: C, 37.92; H, 3.65; Cl, 16.01; N, 6.31; S, 14.47. Found: C, 38.39; H, 3.81; Cl, 15.49; N, 6.31; S, 14.56.

D. 4,5-Dichloro-2-ethyl-4-isothiazolin-3-one

2-Ethyl-3,4,5-trichloroisothiazolium tetrafluoroborate (14.5 g), 0.048 mol) was added in portions to 150 ml of a saturated sodium acetate solution. The aqueous phase was extracted with 3×50 ml of $CH_2Cl_2$. The combined extracts were dried ($MgSO_4$), filtered and concentrated. The oil was distilled to yield 4.2 g (45%) 4,5-dichloro-2-ethyl-4-isothiazolin-3-one, bp 89–92 (0.1 mm).

Analysis: Calculated for $C_5H_5Cl_2NOS$: C, 30.34; H, 2.52; Cl, 35.80; N, 7.07; S, 16.20. Found: C, 30.04; H, 2.59; Cl, 36.14; N, 6.99; S, 15.70.

E. 2-Methyl-4-isothiazolin-3-one

3-Chloro-2-methylisothiazolium fluorosulfonate (39.2 g, 0.17 mol) was added in portions to 100 ml of a saturated sodium acetate solution. The aqueous solution was extracted with 3×50 ml of $CH_2Cl_2$. The combined extracts were dried ($MgSO_4$), filtered and concentrated. The oil was distilled to yield 10.4 g (53%) of 2-methyl-4-isothiazolin-3-one, bp 85° (1.0 mm).

F. 2-Ethyl-4-isothiazolin-3-one

3-Chloro-2-ethylisothiazolium ethylsulfate (15.4 g, 0.56 mol) was added to 75 ml of a saturated sodium acetate solution. The water was removed at reduced pressure and the residue extracted with 3×50 ml of $CH_2Cl_2$. The combined extracts were dried ($MgSO_4$), filtered and concentrated. Distillation yielded 3.6 g (50%) of 2-ethyl-4-isothiazolium-3-one, bp 92 (0.5 mm).

G. 4,5-Dichloro-2-methyl-4-isothiazolin-3-one

2-Methyl-3,4,5-trichloroisothiazoliumfluorosulfonate (5.8 g, 0.02 mol) was added to 100 ml of MeOH and refluxed for 1 hr. The MeOH was removed on a rotary evaporator and the solid collected and washed with water to yield 1.5 g of 4,5-dichloro-2-methyl-4-isothiazolin-3-one.

H. Other 4-Isothiazolin-3-ones

Other 2-alkenyl 4-isothiazolin-3-ones may be similarly prepared from the corresponding salts by methods as illustrated above.

We claim:

1. A salt of the formula:

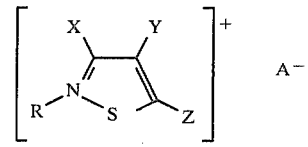

wherein:
R is an alkyl or alkenyl up to 8 carbons;
X is chlorine or bromine;
Y is selected from the group consisting of hydrogen, methyl, ethyl, carbomethoxy, carboethoxy, chlorine, bromine, cyano and nitro;
Z is selected from the group consisting of methyl, ethyl, hydrogen, chlorine, bromine, cyano, carbomethoxy and carboethoxy; and
$A^-$ is a suitable anion.

2. A salt according to claim 1 wherein R is selected from the group of alkyl radicals having one to eight carbon atoms or is an allyl group 3. A salt according to claim 2 wherein:
Y is selected from the group consisting of hydrogen, chlorine, bromine, cyano and nitro; and
Z is selected from the group consisting of hydrogen, chlorine, bromine, cyano, carbomethoxy and carboethoxy.

4. A salt according to claim 3 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

5. A salt according to claim 3 wherein:
R is selected from the group consisting of methyl, ethyl, n-propyl, n-butyl, n-pentyl, n-hexyl, n-heptyl, n-octyl and allyl.

6. A salt according to claim 3 wherein the cationic portion is:

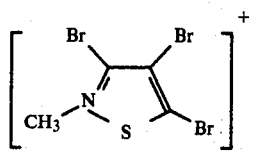

7. A salt according to claim 6 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

8. A salt according to claim 3 wherein X, Y and Z are chlorine.

9. A salt according to claim 8 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

10. A salt according to claim 8 wherein the cationic portion is:

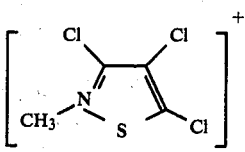

11. A salt according to claim 10 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

12. A salt according to claim 8 wherein the cationic portion is:

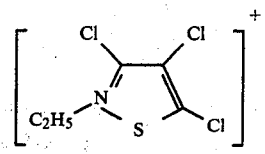

13. A salt according to claim 12 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

14. A salt according to claim 8 wherein the cationic portion is:

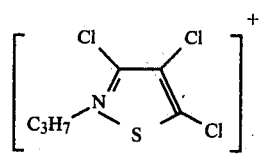

15. A salt according to claim 14 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

16. A salt according to claim 8 wherein the cationic portion is:

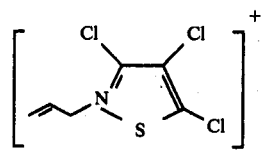

17. A salt according to claim 16 wherein the anion is selected from the group consisting of fluorosulfonate, methylsulfate, hexachloroantimonate, triflroromethanesulfonate, hexafluorophosphate, tetrafluoroborate, ethylsulfate and nitrate.

18. A salt according to claim 8 wherein the cationic portion is:

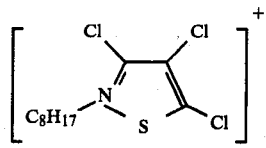

19. A salt according to claim 18 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

20. A salt according to claim 3 wherein:
X is chlorine; and
Y and Z are hydrogen.

21. A salt according to claim 20 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

22. A salt according to claim 20 wherein the cationic portion is:

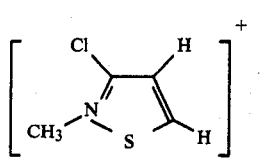

23. A salt according to claim 22 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

24. A salt according to claim 20 wherein the cationic portion is:

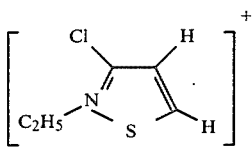

25. A salt according to claim 24 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

26. A salt according to claim 20 wherein the cationic portion is:

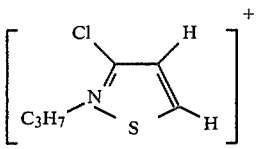

27. A salt according to claim 26 wherein the anion is selected from the group consisting of fluorosulfonate, methyl sulfate, hexachloroantimonate, trifluoromethanesulfonate, hexafluorophosphate, tetrafluoroborate, ethylsulfate and nitrate.

28. A salt according to claim 20 wherein the cationic portion is:

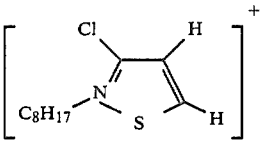

29. A salt according to claim 28 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

30. A salt according to claim 3 wherein X and Y are chlorine.

31. A salt according to claim 30 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

32. A salt according to claim 30 wherein the cationic portion is:

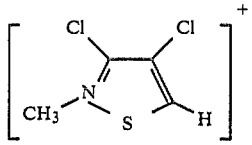

33. A salt according to claim 32 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

34. A salt according to claim 30 wherein the cationic portion is:

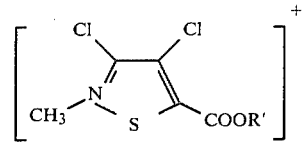

wherein R' is methyl or ethyl.

35. A salt according to claim 34 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

36. A salt according to claim 30 wherein the cationic portion is:

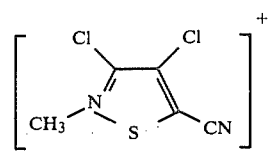

37. A salt according to claim 36 wherein the anion is selected from the group consisting of fluorosulfonate, methylsulfate, hexachloroantimonate, trifluoromethansulfonate, hexafluorophosphate, tetrafluoroborate, ethylsulfate and nitrate.

38. A salt according to claim 30 wherein the cationic portion is:

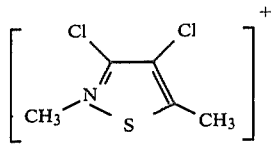

39. A salt according to claim 38 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

40. A salt according to claim 3 wherein the cationic portion is:

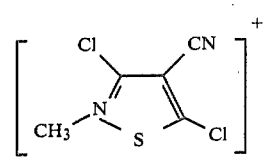

41. A salt according to claim 40 wherein the anion is selected from the group consisting of fluorosulfonate, methylsulfate, hexachloroantimonate, trifluoromethanesulfonate, hexafluorophosphate, tetrafluoroborate, ethylsulfate and nitrate.

42. A salt according to claim 3 wherein the cationic portion is:

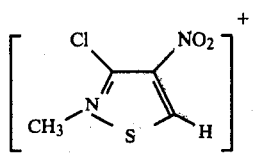
43. A salt according to claim 42 wherein the anion is selected from the group consisting of fluorosulfonate, methylsulfate, hexachloroantimonate, trifluorometh- anesulfonate, hexafluorophosphate, tetrafluoroborate, ethylsulfate and nitrate.
44. A compound of claim 1 having the formula:
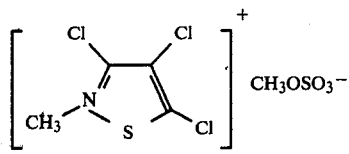
* * * * *